(12) United States Patent
Horiuchi et al.

(10) Patent No.: US 7,495,107 B2
(45) Date of Patent: Feb. 24, 2009

(54) METHOD FOR MANUFACTURING ISOXAZOLE DERIVATIVE OR DIHYDROISOXAZOLE DERIVATIVE

(75) Inventors: C. Akira Horiuchi, Tokyo (JP); Ken-ichi Itoh, Saitama (JP); Noriko Nakazato, Tokyo (JP); Hideo Iwai, Tochigi (JP); Takamitsu Utsukihara, Tokyo (JP); Wen Chai, Tokyo (JP)

(73) Assignee: Rikkyo Gakuin, Tokyo (JP)

( * ) Notice: Subject to any disclaimer, the term of this patent is extended or adjusted under 35 U.S.C. 154(b) by 356 days.

(21) Appl. No.: 11/260,141

(22) Filed: Oct. 28, 2005

(65) Prior Publication Data

US 2006/0247288 A1 Nov. 2, 2006

(30) Foreign Application Priority Data

Apr. 28, 2005 (JP) .............................. 2005-132862
Oct. 3, 2005 (JP) .............................. 2005-290233

(51) Int. Cl.
*C07D 261/08* (2006.01)
*C07D 261/02* (2006.01)
*A61K 31/42* (2006.01)

(52) U.S. Cl. ...................... 548/248; 548/240; 514/378
(58) Field of Classification Search ................ 548/240, 548/241, 247, 248; 514/379, 378
See application file for complete search history.

(56) References Cited

U.S. PATENT DOCUMENTS 4,562,187 A 12/1985 Tegeler et al.

FOREIGN PATENT DOCUMENTS

| JP | 47-29899 | 8/1972 |
| JP | 61-167673 | 7/1986 |
| JP | 3-157375 | 7/1991 |
| WO | 03/074501 | 9/2003 |
| WO | 2004/014370 | 2/2004 |

OTHER PUBLICATIONS

Ken-ichi Itoh, et al., A Convenient and Efficient One-Pot Synthesis of 3-Acylisoxazoles Using Iron(III) Salts, 2005, Synthesis, No. 20, pp. 3541-3548.*
Ken-ichi Itoh et al., "Formation of isoxazole derivatives via nitrile oxide using ammonium cerium nitrate (CAN): a novel one-pot synthesis of 3-acetyl- and 3-benzoylisoxazole derivatives", Tetrahedron, 60, pp. 1671-1681, 2004.
Ken-ichi Itoh et al., "A novel one-pot synthesis of 3-acetyl- and 3-benzoylisoxazole derivatives using ammonium cerium nitrate (CAN)", Tetrahedron Letters, 43, pp. 7035-7037, 2002.
"SciFinder Scholar" searched on Jun. 18, 2005, pp. 2-4.
"SciFinder Scholar" searched on Jun. 18, 2005, pp. 2-15.
Giorgio Gaudiano et al., "Synthesis of 5-ethoxyisoxazoles", Chemical Abstracts, vol. 55, No. 7, abstract No. 6467c, 1961.
Zhurnal Obshchei Khimii, vol. 45, No. 12, pp. 2609-2614, 1975.

* cited by examiner

*Primary Examiner*—Kamal A Saeed
*Assistant Examiner*—Kristin Bianchi
(74) *Attorney, Agent, or Firm*—Wenderoth, Lind & Ponack, L.L.P.

(57) ABSTRACT

There is provided with a method for manufacturing an isoxazole derivative at a high yield and without discharging waste products, and a novel isoxazole derivative. An isoxazole derivative expressed by Formula (8) is produced by reacting a 1-alkyne compound expressed by Formula (7) with iron(III) nitrate in the presence of acetone or acetophenone:

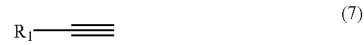

(where $R_1$ is an alkyl, cycloalkyl, phenyl, or other such group); and

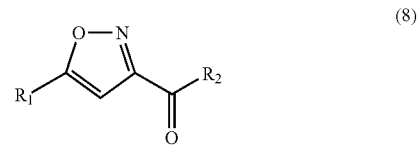

(where $R_2$ is a methyl or a phenyl).

4 Claims, No Drawings

METHOD FOR MANUFACTURING ISOXAZOLE DERIVATIVE OR DIHYDROISOXAZOLE DERIVATIVE

BACKGROUND OF THE INVENTION

1. Field of the Invention

The present invention relates to a method for manufacturing an isoxazole derivative or a dihydroisoxazole derivative, and more particularly relates to a novel method for manufacturing an isoxazole derivative or a dihydroisoxazole derivative in which iron(III) nitrate is utilized, which results in a higher yield and no waste being discharged, and to novel isoxazole derivatives obtained by the manufacturing method.

2. Description of Related Art

Isoxazole derivatives are known to be compounds that have various pharmacological actions, such as anticancer action, anti-inflammatory action, and immunomodulatory action. Meanwhile, an isoxazole ring, which is a heterocycle, is a reaction intermediate that is useful in the pharmaceutical field and in organic synthesis because it can be converted by reductive ring cleavage into α, β unsaturated ketone, β-diketone, β-hydroxyketone, and γ-amylalcohol. In view of this, it would likely be extremely significant if a method could be developed for more efficiently synthesizing these isoxazole derivatives.

Up to now the construction of these heterocycles relied upon a method that went from a ketone compound through an oxime to a nitrile oxide, and involved 1,3-cycloaddition.

It is also known that when cerium(IV) ammonium nitrate (commonly referred to as CAN(IV)) is allowed to act on an alkene or an alkyne, which are compounds having carbon-carbon unsaturated double or triple bonds, at 80° C. in acetophenone or under reflux in acetone, this results in the nitration of the solvent molecules and the production of nitrile oxide, and then a 1,3-dipolar cycloaddition reaction gives an isoxazole derivative at a high yield and in a single step, and that when nitric acid and CAN(III) are used instead of CAN (IV), the same reaction occurs, fewer by-products are produced, and the yield is even higher (see, for example, K. Itoh, S. Takahashi, T. Ueki, T. Takahashi, and C. A. Horiuchi, *Tetrahedron Letters*, 43 (2002), pp. 7035-7037, and K. Itoh and C. A. Horiuchi, *Tetrahedron*, 60 (2004), pp. 1671-1681).

SUMMARY OF THE INVENTION

However, with a synthesis method such as those described in *Tetrahedron Letters*, 43 (2002), pp. 7035-7037 and *Tetrahedron*, 60 (2004), pp. 1671-1681, which make use of cerium (IV) ammonium nitrate or cerium(III) ammonium nitrate, waste products and so forth that lead to environmental pollution are discharged, disposing of these waste products drives up the cost, and the yield was not necessarily satisfactory, among several other problems.

In view of this situation, the inventors felt that the reaction would probably occur if a nitrate other than a cerium nitrate were used, and they investigated nitrates of a variety of metals. As a result, they found that the same reaction occurs when using iron(III) nitrate, which is a metal salt that is less costly than a cerium salt and is more environmentally friendly because its by-products are easier to process.

It is an object of the present invention to provide a novel method for manufacturing isoxazole derivatives at a high yield and without producing any waste materials.

It is another object of the present invention to provide a novel isoxazole derivative from an alkyne compound utilizing iron(III) nitrate.

(i) According to a first aspect of the present invention, there is provided a method for manufacturing a dihydroisoxazole derivative, in which a dihydroisoxazole derivative expressed by Formula (2) is obtained or formed by reacting a 1-alkene compound expressed by Formula (1), with iron(III) nitrate in the presence of acetone or acetophenone:

(1)

(where $R_1$ is a linear or branched alkyl group that may have a substituent, a cycloalkyl group that may have a substituent, an alkoxyl group that may have a substituent, an alkoxycarbonyl group that may have a substituent, an alkylcarboxyl group that may have a substituent, an alkylthio group that may have a substituent, an alkylsulfonyl group that may have a substituent, a phenyl group that may have a substituent, a naphthyl group that may have a substituent, a phenoxy group that may have a substituent, an aromatic or non-aromatic heterocyclic group that may have a substituent, an alkylamino group that may have a substituent, an alkylcyano group that may have a substituent, a nitro group that may have a substituent, or an acyl group that may have a substituent); and

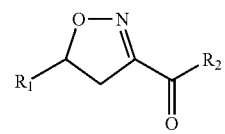

(2)

(where $R_1$ is defined the same as above, and $R_2$ is a methyl group or a phenyl group).

(ii) According to a feature of the preferred embodiment of the present invention, the 1-alkene compound is a 1-alkene compound expressed by Formula (3):

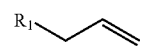

(3)

(where $R_1$ is defined the same as above); and
the dihydroisoxazole derivative is a dihydroisoxazole derivative expressed by Formula (4):

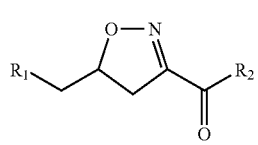

(4)

(where $R_1$ and $R_2$ are defined the same as above).

(iii) According to a feature of the preferred embodiment of the present invention, the 1-alkene compound is a cyclic alkene compound expressed by Formula (5):

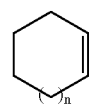

(5)

(where n is an integer from 0 to 3); and the dihydroisoxazole derivative is expressed by Formula (6):

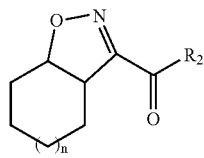
(6)

(where $R_2$ and n are defined the same as above).

(iv) According to a feature of the preferred embodiment of the present invention, the reaction is conducted under microwave irradiation.

(v) According to a feature of the preferred embodiment of the present invention, the dihydroisoxazole derivative is a 3-acetylisoxazole derivative.

(vi) According to a feature of the preferred embodiment of the present invention, the dihydroisoxazole derivative is a 3-benzoylisoxazole derivative.

(vii) According to a second aspect of the present invention, there is provided a method for manufacturing an isoxazole derivative, in which an isoxazole derivative expressed by Formula (8) is obtained or formed by reacting a 1-alkyne compound expressed by Formula (7) with iron(III) nitrate in the presence of acetone or acetophenone:

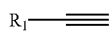
(7)

(where $R_1$ is defined the same as above); and

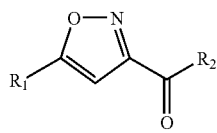
(8)

(where $R_1$ and $R_2$ are defined the same as above).

(viii) According to a third aspect of the present invention, there is provided a method for manufacturing an isoxazole derivative, in which an isoxazole derivative expressed by Formula (10) is obtained or formed by reacting an ethynyltestosterone compound expressed by Formula (9) with iron (III) nitrate under microwave irradiation in the presence of acetone or acetophenone:

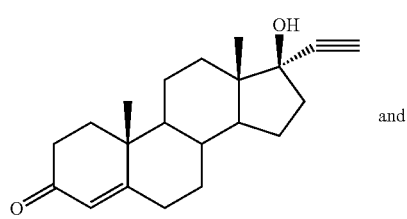
(9)

and

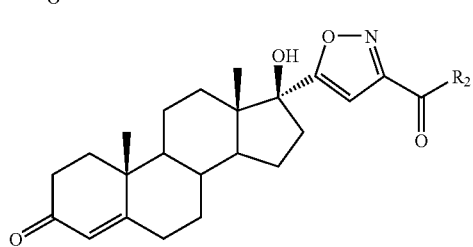
(10)

(where $R_2$ is defined the same as above).

(ix) According to a fourth aspect of the present invention, there is provided an isoxazole derivative expressed by Formula (8):

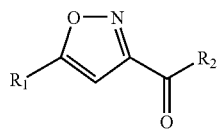
(8)

(where $R_1$ and $R_2$ are defined the same as above, excluding a case in which $R_1$ is a methyl group or a phenyl group).

(x) According to a fifth aspect of the present invention, there is provided an isoxazole derivative expressed by Formula (10):

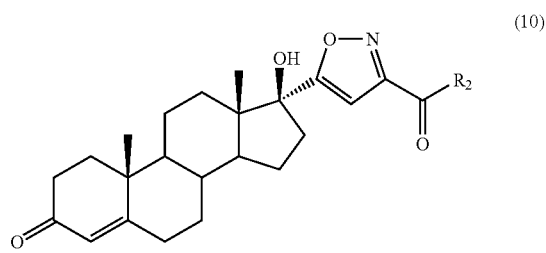
(10)

(where $R_2$ is defined the same as above).

(xi) According to a feature of the preferred embodiment of the present invention, the above-mentioned isoxazole derivative according to the item (ix) or (x) is a 3-acetylisoxazole derivative or a 3-benzoylisoxazole derivative.

(xii) According to a feature of the preferred embodiment of the present invention, the above-mentioned isoxazole derivative according to the item(ix) is 3-acetyl-5-butylisoxazole, 3-acetyl-5-pentylisoxazole, 3-acetyl-5-hexylisoxazole, 3-benzoyl-5-propylisoxazole, 3-benzoyl-5-butylisoxazole, 3-benzoyl-5-pentylisoxazole, or 3-benzoyl-5-hexylisoxazole.

(xiii) According to a feature of the preferred embodiment of the present invention, the above-mentioned isoxazole derivative according to the item (x) is 3-acetyl-6-hydroxy-5-cyclohexylisoxazole.

With the inventions constituted as described in the items (i) to (iii), (v) and (vi), the iron(III) nitrate used in the reaction is a metal salt that is inexpensive and environmentally friendly, and is an excellent reagent that is easy to process, so the benefits of using this substance are that it does not harm the environment, and although the reaction takes slightly longer than when a cerium salt is used, the isoxazole derivative that is the target compound is obtained at a higher yield. Also, an isoxazole ring can be synthesized in a single step. Further, the target compound can be obtained at a higher yield when acetophenone is used than when acetone is used. Also, the target compound can be obtained at a high yield without having to process any waste products.

With the invention constituted as described in the item (iv), in addition to the above-mentioned advantageous effects, the reaction time can be shortened even when synthesizing an alkene compound, which takes longer for the reaction, and the yield can be raised.

With the invention constituted as described in the item (vii), the advantageous effect is that a novel compound having a pharmacological action can be synthesized at a better yield than when no microwave irradiation is used during reaction.

With the invention constituted as described in the item (viii), the advantageous effect is that the microwaves promote the reaction, and a novel compound having a pharmacological action can be produced efficiently in a short time.

With the inventions constituted as described in the items (ix) to (xiii), the advantageous effect is that an isoxazole derivative with a novel structure that is useful and has a pharmacological action can be provided.

DESCRIPTION OF THE PREFERRED EMBODIMENTS

The various constituent requirements of the method of the present invention for manufacturing an isoxazole derivative will now be described in detail.

With the manufacturing method of the present invention, the 1-alkene compound expressed by the above-mentioned Formula (1) or Formula (7) is reacted with iron(III) nitrate, and this reaction is conducted in the presence of acetone or acetophenone. In particular, when an ethynyltestosterone compound is used, the reaction is conducted under microwave irradiation.

With another manufacturing method of the present invention, the ethynyltestosterone compound expressed by the above-mentioned Formula (9) is reacted with iron(III) nitrate.

Further, $R_1$ in the above-mentioned Formulas (1) to (8) of the 1-alkene compound and 1-alkyne compound that can be used in the present invention is a linear or branched alkyl group that may have a substituent, a cycloalkyl group that may have a substituent, an alkoxy group that may have a substituent, an alkoxycarbonyl group that may have a substituent, an alkylcarboxyl group that may have a substituent, an alkylthio group that may have a substituent, an alkylsulfonyl group that may have a substituent, a phenyl group that may have a substituent, a naphthyl group that may have a substituent, a phenoxy group that may have a substituent, an aromatic or non-aromatic heterocyclic group that may have a substituent, an alkylamino group that may have a substituent, an alkylcyano group that may have a substituent, a nitro group that may have a substituent, or an acyl group that may have a substituent.

Examples of the above-mentioned substituent include halogen atoms such as fluorine, chlorine, bromine, and iodine; a nitro group; a cyano group; methyl, ethyl, propyl, butyl, isobutyl, sec-butyl, t-butyl, pentyl, and other such alkyl groups, which may be substituted; cyclobutyl, cyclopentyl, cyclohexyl, and other such cycloalkyl groups, which may be substituted; a methylthio group, which may be substituted; a phenyl group, which may be substituted; 1-naphthyl, 2-naphthyl, and other such naphthyl groups; 1-pyrrolidyl, piperidinyl, morpholino, and other such non-aromatic heterocyclic groups, which may be substituted; 2-furyl, 3-furyl, 2-thienyl, 2-pyridyl, 1-pyrrolyl, 1-imidazolyl, 1-pyrazolyl, and other such aromatic heterocyclic groups, which may be substituted; methoxy, ethoxy, propoxy, butoxy, hexyloxy, nonyloxy, and other such alkoxy groups, which may be substituted; carboxyl groups, which may be substituted; alkoxycarbonyl groups, which may be substituted; acetyl, propionyl, butyryl, benzoyl, and other such acyl groups, which may be substituted; methylamino, ethylamino, diethylamino, acetylamino, benzoylamino, phenylamino, and other such amino groups, which may be substituted; methoxy, ethoxy, propoxy, butoxy, isobutoxy, sec-butoxy, t-butoxyhexyloxy, and other such hydroxyl groups, which may be substituted; ethylthio, cyclobutylthio, phenylthio, 2-pyridinethio, and other such thiol groups; and carbonyl, ethoxycarbonyl, and other such carboxyl groups, which may be esterified or amidated.

Favorable examples of the linear or branched alkyl group that may have a substituent in the definition of $R_1$ in the above-mentioned Formulas (1) to (8) of the 1-alkene compound and 1-alkyne compound which can be used in the present invention are alkyl groups having carbon number 1 to 12, with alkyl groups having carbon number 3 to 9 being particularly favorable.

Specific examples of said alkyl groups include a methyl group, trifluoromethyl group, trichloromethyl group, dichloromethyl group, iodomethyl group, bromomethyl group, ethyl group, 2,2,2-trifluoroethyl group, 2,2,2-trichloroethyl group, pentafluoroethyl group, n-propyl group, isopropyl group, n-butyl group, isobutyl group, sec-butyl group, t-butyl group, n-pentyl group, isoamyl group, n-hexyl group, n-heptyl group, 1-methylhexyl group, 3-methylhexyl group, 4-methylhexyl group, 5-methylhexyl group, 1-ethylpentyl group, 1,1-diethylpentyl group, 1,4-diethylpentyl group, 1,1-diethylpropyl group, 1,3,3-trimethylbutyl group, 1-ethyl-2,2-dimethylpropyl group, n-octyl group, 1-methylheptyl group, 1-ethylhexyl group, 2-ethylhexyl group, 1-propylpentyl group, 1,1-dimethylhexyl group, 1-ethyl-1-methylpentyl group, 2,4,4-trimethylpentyl group, 1,1,3,3-tetrramethylbutyl group, n-nonyl group, 1-methyloctyl group, 1-ethylheptyl group, 1,5,5-trimethylhexyl group, n-decyl group, 1-methylnonyl group, 1,1-dimethyloctyl group, 3,7-dimethyloctyl group, n-undecanyl group, 1-methyldecyl group, and n-dodecyl group.

Favorable examples of the cycloalkyl group that may have a substituent in the definition of $R_1$ in the above-mentioned Formulas (1) to (8) of the 1-alkene compound and 1-alkyne compound which can be used in the present invention are cycloalkyl groups having carbon number 3 to 10, with cycloalkyl groups having carbon number 5 and 6 being particularly favorable.

Specific examples of said cycloalkyl groups include a cyclopropyl group, cyclobutyl group, cyclopentyl group, cyclohexyl group, cycloheptyl group, cyclooctyl group, [2.2.1]heptyl group, and [2.2.2]octyl group.

Favorable examples of the alkoxyl group that may have a substituent in the definition of $R_1$ in the above-mentioned Formulas (1) to (8) of the 1-alkene compound and 1-alkyne compound which can be used in the present invention are alkoxyl groups having carbon number 1 to 6, with alkoxyl groups having carbon number 2 to 6 being particularly favorable.

Specific examples of said alkoxyl groups include a methoxy group, trifluoromethoxy group, trichloromethoxy group, dichloromethoxy group, ethoxy group, bromoethoxy group, 2-iodoethoxy group, 2,2,2-trichloroethoxy group, propoxy group, 3-chloropropoxy group, butoxy group, and pentoxy group.

Favorable examples of the alkylthio group that may have a substituent in the definition of $R_1$ in the above-mentioned Formulas (1) to (8) of the 1-alkene compound and 1-alkyne compound which can be used in the present invention are alkylthio groups having carbon number 1 to 6, with alkylthio groups having carbon number 1 to 3 being particularly favorable.

Specific examples of said alkylthio groups include a methylthio group, ethylthio group, n-propylthio group, 1-methylethylthio group, n-butylthio group, 1-methylpropylthio group, 1,1-dimethylpropylthio group, 2,2-dimethylpropylthio group, n-pentylthio group, 2-methylbutylthio group, and n-hexylthio group.

Favorable examples of the alkylcyano group that may have a substituent in the definition of $R_1$ in the above-mentioned Formulas (1) to (8) of the 1-alkene compound and 1-alkyne compound which can be used in the present invention are alkylcyano groups having no carbon or having carbon number 1 to 6, with alkylcyano groups having no carbon or having carbon number 1 to 3 being particularly favorable.

Specific examples of said alkylcyano groups include a cyano group, methylcyano group, ethylcyano group, and n-propylcyano group.

Favorable examples of the alkylsulfonyl group that may have a substituent in the definition of $R_1$ in the above-mentioned Formulas (1) to (8) of the 1-alkene compound and 1-alkyne compound which can be used in the present invention are alkylsulfonyl groups having carbon number 1 to 6.

Specific examples of said alkylsulfonyl groups include a methylsulfonyl group, ethylsulfonyl group, n-propylsulfonyl group, 1-methylethylsulfonyl group, n-butylsulfonyl group, 1-methylpropylsulfonyl group, n-pentylsulfonyl group, 2-methylbutylsulfonyl group, n-hexylsulfonyl group, and 1-ethylbutylsulfonyl group.

Favorable examples of the alkoxycarbonyl group that may have a substituent in the definition of $R_1$ in the above-mentioned Formulas (1) to (8) of the 1-alkene compound and 1-alkyne compound which can be used in the present invention are alkoxycarbonyl groups having carbon number 1 to 7.

Specific examples of said alkoxycarbonyl groups include a methoxycarbonyl group, ethoxycarbonyl group, n-propoxycarbonyl group, n-butoxycarbonyl group, t-butoxycarbonyl group, isoamyloxycarbonyl group, and n-hexyloxycarbonyl group.

Favorable examples of the alkylcarboxyl group that may have a substituent in the definition of $R_1$ in the above-mentioned Formulas (1) to (8) of the 1-alkene compound and 1-alkyne compound which can be used in the present invention are alkylcarboxyl groups having carbon number 2 to 6.

Specific examples of said alkylcarboxyl groups include a methylcarboxyl group, ethylcarboxyl group, n-propylcarboxyl group, 1-methylethylcarboxyl group, n-butylcarboxyl group, 1-methylpropylcarboxyl group, n-pentylcarboxyl group, 2-methylbutylcarboxyl group, n-hexylcarboxyl group, and 1-ethylbutylcarboxyl group.

Favorable examples of the phenyl group that may have a substituent in the definition of $R_1$ in the above-mentioned Formulas (1) to (8) of the 1-alkene compound and 1-alkyne compound which can be used in the present invention are phenyl groups having carbon number 6 to 14, with phenyl groups having carbon number 6 to 10 being particularly favorable.

Specific examples of said phenyl groups include a phenyl group, o-tolyl group, m-tolyl group, p-tolyl group, p-ethylphenyl group, p-isopropylphenyl group, p-t-butylphenyl group, p-chlorophenyl group, p-methoxyphenyl group, and p-butoxyphenyl group.

Favorable examples of the naphthyl group that may have a substituent in the definition of $R_1$ in the above-mentioned Formulas (1) to (8) of the 1-alkene compound and 1-alkyne compound which can be used in the present invention are naphthyl groups having carbon number 10 to 17, with naphthyl groups having carbon number 10 to 12 being particularly favorable.

Specific examples of said naphthyl groups include a 1-naphthyl group, 2-naphthyl group, 6-methyl-2-naphthyl group, and 6-chloro-2-naphthyl group.

Favorable examples of the phenoxy group that may have a substituent in the definition of $R_1$ in the above-mentioned Formulas (1) to (8) of the 1-alkene compound and 1-alkyne compound which can be used in the present invention are phenoxy groups having carbon number 6 to 14, with phenoxy groups having carbon number 6 to 10 being particularly favorable.

Specific examples of said phenoxy groups include a phenoxy group.

Favorable examples of the aromatic or non-aromatic heterocyclic group that may have a substituent in the definition of $R_1$ in the above-mentioned Formulas (1) to (8) of the 1-alkene compound and -alkyne compound which can be used in the present invention are aromatic or non-aromatic heterocyclic groups of a five- to seven-member ring, with aromatic or non-aromatic heterocyclic groups of a five- or six-member ring being particularly favorable.

Specific examples of said aromatic or non-aromatic heterocyclic groups include a 1-pyrrolidinyl group, piperidinyl group, morpholinyl group, piperazinyl group, furyl group, thienyl group, pyridyl group, pyrimidinyl group, pyrazinyl group, pyrrolyl group, imidazolyl group, pyrazolyl group, oxazolyl group, thiazolyl group, benzoxazolyl group, benzimidazolyl group, and benzthiazolyl group.

Favorable examples of the alkylamino group that may have a substituent in the definition of $R_1$ in the above-mentioned Formulas (1) to (8) of the 1-alkene compound and 1-alkyne compound which can be used in the present invention are alkylamino groups having no carbon or having carbon number 1 to 13, with alkylamino groups having no carbon or having carbon number 1 to 10 being particularly favorable.

Specific examples of said alkylamino groups include an amino group, methylamino group, ethylamino group, and dibutylamino group.

Favorable examples of the acyl group that may have a substituent in the definition of $R_1$ in the above-mentioned Formulas 1 to 8 of the 1-alkene compound and 1-alkyne compound which can be used in the present invention are acyl groups having carbon number 2 to 13, with acyl groups having carbon number 2 to 7 being particularly favorable.

Specific examples of said acyl groups include an acetyl group, propionyl group, butyryl group, hexanoyl group, and benzoyl group.

The reaction temperature that can be used in the present invention can be appropriately selected according to the type of substrate and other such factors, but is preferably from 50 to 150° C., with approximately 56 to 80° C. being particularly favorable. Usually, however, when acetone is used as the solvent, the reaction is preferably conducted under acetone reflux, and when acetophenone is used, the reaction is preferably conducted at 80° C. It is undesirable for the reaction temperature to be either over or under the above range because it will be impossible to obtain the targeted isoxazole derivative at a high yield.

The reaction can be conducted under at working or atmospheric pressure or under pressurization. When the reaction is conducted under pressurization, the pressure is preferably from 2 to 16 bar, and approximately 15 bar is particularly favorable. It is undesirable for the pressurization to be either over or under the above range because the yield will decrease.

The reaction time that can be used in the present invention is determined according to the reaction temperature and pressure, but, for example, approximately 10 to 50 hours is favorable, with 15 to 25 hours being preferable. It is undesirable for the reaction to last less than 10 hours or more than 50 hours because the yield will decrease.

When microwaves are used in the present invention, their output is preferably from 90 to 250 watts (W). The pressure thereof is preferably from 2 to 16 bar, and approximately 15 bar is particularly favorable. It is undesirable for the output and pressure of the microwaves to be outside the above ranges because no increase in yield can be achieved.

The amount in which the iron(III) nitrate is used in the present invention is preferably from 0.5 to 4.0 molar equivalents, and even more preferably from 1.0 to 1.5 molar equivalents, and ideally 1.0 molar equivalent, with respect to the substrate. It is undesirable for the amount used to be outside the above range because the yield will decrease.

The solvents that can be used in the reaction in the present invention are acetone and acetophenone, but the targeted isoxazole derivative can be obtained at a higher yield when acetophenone is used than when acetone is used.

WORKING EXAMPLES

Embodiments of the present invention will now be described in more specific terms through working examples, but insofar as its gist is not exceeded, the present invention is not limited to the scope described in these working examples.

The substrate, iron(III) nitrate, copper(II) nitrate, aluminum nitrate, magnesium nitrate, ammonium nitrate, and carbonyl compounds used in these working examples of the present invention were all commercially available products.

The following measurement apparatus were used to measure the structure, properties, and so forth of the isoxazole derivative that is the product of the present invention.

IR: FT-IR-230, made by JASCO Corporation
NMR: JEOL GSX400, made by JEOL
GC: Shimadzu Gas Chromatograph GC-17A, made by Shimadzu
GC-MS: GCMS-QP5050, made by Shimadzu
GCL: HP5890, made by Hewlett Packard Experimental Methodology 0.1 mol of substrate and 0.1 mol of iron(III) nitrate were reacted in 40 mL of acetone or acetophenone, either under reflux or at 80° C., while the system was stirred. Upon completion of the reaction, the iron was filtered off with High-Flow Super Cell, and the reaction mixture was extracted with 50 mL of diethyl ether. This extract was then washed first with saturated sodium hydrogencarbonate, then with saturated salt water, then with distilled water. The ether layer was dried and concentrated with anhydrous sodium sulfate. When acetophenone was used, it was distilled off at this point under reduced pressure. The pale yellow, oily substance thus obtained was isolated and purified by silica gel chromatography, and the NMR, IR, GC-MS, and other spectra were measured to determine the structure of the product.

Working Examples 1 to 8

(1) Reacting acetone or acetophenone with chain-form 1-alkene compound using iron(III) nitrate Iron(III) nitrate was made to act in acetone or acetophenone, using a chain-form 1-alkene compound as the substrate (1-hexene (hereinafter "substrate 1"), 1-heptene ("substrate 2"), 1-octene ("substrate 3"), 1-dodecene ("substrate 4")).

As a result, as shown in Table 1 below, it was found that isoxazole derivatives (1a-4a, 1b-4b) were obtained at a higher yield than when cerium(IV) ammonium nitrate (CAN(IV)), which is a conventional metal nitrate, was used.

For almost all the substrates, the yield was higher when acetophenone was used than when acetone was used, the reason for which will be discussed below.

The following abbreviations used in the tables in this Specification refer to the following groups.
Me: methyl group
pH: phenyl group

TABLE 1

Reaction between 1-alkene compound and $Fe(NO_3)_3$ in acetone or acetophenone $$R_1 \diagdown \xrightarrow[\text{solvent}]{Fe(NO_3)_3} R_1 \diagdown \text{(isoxazoline structure)} R_2$$

1, 2, 3, 4      (1a-4a, 1b-3b)

1: $R_1$ = n-$C_4H_8$    a: $R_2$ = $CH_3$
2: $R_1$ = n-$C_5H_{11}$   b: $R_2$ = $C_6H_5$
3: $R_1$ = n-$C_6H_{13}$
4: $R_1$ = n-$C_9H_{19}$

| Working Example[a] | Substrate | Solvent | Temp. (°C.) | Time (hours) | Product (%)[b] | CAN (IV) (%) |
|---|---|---|---|---|---|---|
| 1 | 1 | $Me_2CO$ | reflux | 25 | 1a (77) | (67) |
| 2 | 2 | $Me_2CO$ | reflux | 25 | 2a (77) | (72) |
| 3 | 3 | $Me_2CO$ | reflux | 25 | 3a (85) | (72) |
| 4 | 4 | $Me_2CO$ | reflux | 25 | 4a (75) | (63) |
| 5 | 1 | PhCOMe | 80 | 25 | 1b (77) | (68) |
| 6 | 2 | PhCOMe | 80 | 25 | 2b (92) | (78) |
| 7 | 3 | PhCOMe | 80 | 25 | 3b (95) | (77) |
| 8 | 4 | PhCOMe | 80 | 25 | 4b (85) | (72) |

[a] Reaction conditions: 0.5 mmol substrate, 0.5 mmol $Fe(NO_3)_3$, 3.0 mL solvent
[b] Yield: GLC yield (%)

Working Examples 9 to 20

(2) Reacting acetone or acetophenone with various alkene compounds using iron(III) nitrate In order to how widely applicable this reaction is, a test was conducted under the same reaction conditions using substrates having various substituents at the allyl position (allylcyclohexane ("substrate 5"), allylbenzene ("substrate 6"), allyl sulfide ("substrate 7"), allyl cyanide ("substrate 8"), allyl phenyl ether ("substrate 9"), and allyl acetate ("substrate 10").

As a result, as shown in Table 2 below, the yield was somewhat lower with some of the compounds than in the reaction with a chain-form 1-alkene compound, but it was confirmed that the reaction proceeded even when the side chain was not an alkane. It is possible that this fluctuation in yield is due to the presence of hetero atoms at the allyl position, causing the reactivity of double bonds to vary, which is unlike the situation with the chain-form 1-alkene compounds. It was clear that the yield was higher with almost all of the substrates than when cerium(IV) ammonium nitrate (CAN (IV)), which is a conventional metal nitrate, was used.

TABLE 2

Reaction between various 1-alkene compounds and $Fe(NO_3)_3$ in acetone or acetophenone $$R_1 \diagup\!\!\diagdown \xrightarrow[\text{solvent}]{Fe(NO_3)_3} R_1 \diagup\!\!\diagdown\!\!\diagup\!\!\diagdown\binom{O-N}{}\!\!-\!\!C(=O)R_2$$

5-10 → (5a-10a, 5b-10b)

5: $R_1 = C_6H_{11}$    a: $R_2 = CH_3$
6: $R_1 = C_6H_5$    b: $R_2 = C_6H_5$
7: $R_1 = SCN_3$
8: $R_1 = CN$
9: $R_1 = OC_5H_6$
10: $R_1 = OCOCH_3$

| Working Example[a] | Substrate | Solvent | Temp. (°C.) | Time (hours) | Product (%)[b] | CAN (IV) (%) |
|---|---|---|---|---|---|---|
| 9  | 5  | Me₂CO  | reflux | 20 | 5a (79)  | (69) |
| 10 | 6  | Me₂CO  | reflux | 20 | 6a (80)  | (72) |
| 11 | 7  | Me₂CO  | reflux | 15 | 7a (49)  | (33) |
| 12 | 8  | Me₂CO  | reflux | 18 | 8a (68)  | (55) |
| 13 | 9  | Me₂CO  | reflux | 18 | 9a (70)  | (29) |
| 14 | 10 | Me₂CO  | 80     | 18 | 10a (53) | (44) |
| 15 | 5  | PhCOMe | 80     | 24 | 5b (87)  | (67) |
| 16 | 6  | PhCOMe | 80     | 24 | 6b (88)  | (54) |
| 17 | 7  | PhCOMe | 80     | 15 | 7b (56)  | (18) |
| 18 | 8  | PhCOMe | 80     | 20 | 8b (89)  | (60) |
| 19 | 9  | PhCOMe | 80     | 20 | 9b (79)  | (39) |
| 20 | 10 | PhCOMe |        | 20 | 10b (90) | (66) |

[a]Reaction conditions: 0.5 mmol substrate, 0.5 mmol $Fe(NO_3)_3$, 3.0 mL solvent
[b]Yield: GLC yield (%)

Working Examples 21 to 26

(3) Reacting acetone or acetophenone with cyclic alkene compound using iron(III) nitrate Taking into account steric hindrance to the substituent in the 3-position of the isoxazole ring for the products obtained from the various 1-alkenes discussed above, it was hoped that if the alkene compound were given a cyclic structure to reduce the steric effect on the substituent in the 3-position of the isoxazole ring, the reaction would proceed even with a cyclic alkene, which allows steric hindrance due to rotation of single bonds to be minimized, and the following test was conducted to confirm this. The reaction was conducted using as the substrate cyclohexene ("substrate 17"), cycloheptene ("substrate 18"), and cyclooctene ("substrate 19").

As a result, as shown in Table 3, the reaction proceeded and a dicyclic product (17a-19a, 17b-19b) sharing the 4- and 5-positions of the isoxazole ring could be obtained at a high yield.

TABLE 3

Reaction between cycloalkene compound and $Fe(NO_3)_3$ in acetone or acetophenone 17-19 → (17a-19a, 17b-19b)

17: n = 1    a: $R_2 = CH_3$
18: n = 2    b: $R_2 = C_6H_5$
19: n = 3

| Working Example[a] | Substrate | Solvent | Temp. (°C.) | Time (hours) | Product (%)[b] | CAN (IV) (%) |
|---|---|---|---|---|---|---|
| 21 | 17 | Me₂CO  | reflux | 20 | 17a (33) | (22) |
| 22 | 18 | Me₂CO  | reflux | 15 | 18a (80) | (56) |
| 23 | 19 | Me₂CO  | reflux | 15 | 19a (83) | (59) |
| 24 | 17 | PhCOMe | 80     | 20 | 17b (90) | (49) |
| 25 | 18 | PhCOMe | 80     | 15 | 18b (64) | (57) |
| 26 | 19 | PhCOMe | 80     | 15 | 19b (82) | (71) |

[a]Reaction conditions: 0.5 mmol substrate, 0.5 mmol $Fe(NO_3)_3$, 3.0 mL solvent
[b]Yield: GLC yield (%)

Working Examples 27 to 36

(4) In Working Examples 27 to 36, microwave irradiation was performed in a reaction between 0.5 mmol of 1-octene and 3.0 mL of acetone using 0.5 mmol of iron(III) nitrate. The microwave power was between 80 and 130 watts (W), the pressure was 15 bar, and the temperature was 60° C.

As a result, increases in yield were seen as shown in Table 4 below.

TABLE 4

Application of microwaves in reaction between 1-octene and $Fe(NO_3)_3$ in acetone 1 → 1a 1, 1a: $R_1 = n\text{-}C_6H_{13}$, $R_2 = Me$

| Working Example[a] | Watts | Time (minutes) | Product (%)[b] |
|---|---|---|---|
| 27 | 80  | 20 | 1a (19) |
| 28 | 90  | 20 | 1a (44) |
| 29 | 100 | 20 | 1a (45) |
| 30 | 110 | 20 | 1a (56) |
| 31 | 120 | 20 | 1a (76) |
| 32 | 130 | 20 | 1a (53) |
| 33 | 120 | 10 | 1a (34) |
| 34 | 120 | 30 | 1a (79) |
| 35 | 120 | 40 | 1a (75) |
| 36 | 120 | 50 | 1a (72) |

[a]Reaction conditions: 0.5 mmol 1-octene, 0.5 mmol $Fe(NO_3)_3$, 3.0 mL acetone solvent
[b]Yield: GLC yield (%)

Working Examples 37 to 48

(5) Reacting acetone or acetophenone with 1-alkyne compound using iron(III) nitrate It has been reported that isoxazole derivative have been synthesized from a certain type of alkyne compound obtained using cerium ammonium nitrate (CAN), and tests were therefore conducted in the hope that the same reaction would proceed when iron(III) nitrate was used instead of cerium ammonium nitrate (CAN). These tests were conducted using as the substrate 1-pentyne ("substrate 11"), 1-hexyne ("substrate 12"), 1-heptyne ("substrate 13"), 1-octyne ("substrate 14"), ethynyl propanoate ("substrate 15"), and 1-ethynyl-1-cyclohexanol ("substrate 16"), and as a result it was confirmed that the reaction did indeed proceed.

These results are given in Table 5 below. Just as with an alkene compound, it was found that the targeted isoxazole derivative was obtained at a higher yield than when cerium ammonium nitrate (CAN) was used.

TABLE 5

Reaction between 1-alkyne compound and $Fe(NO_3)_3$ in acetone or acetophenone $R_1$—≡— $\xrightarrow{Fe(NO_3)_3, \text{solvent}}$ isoxazole product 11-16 (11a-16a, 11b-16b)

11: $R_1$ = n-$C_3H_7$    a: $R_2$ = n-$CH_3$
12: $R_1$ = n-$C_4H_9$    b: $R_2$ = n-$C_6H_5$
13: $R_1$ = n-$C_5H_{11}$
14: $R_1$ = n-$C_6H_{13}$
15: $R_1$ = $OCOC_2H_5$
16: $R_1$ = Cy-$C_6H_{11}OH$

| Working Example[a] | Substrate | Solvent | Temp. (° C.) | Time (hours) | Product (%)[b] | CAN (IV) (%) |
|---|---|---|---|---|---|---|
| 37 | 11 | $Me_2CO$ | reflux | 18 | 11a (55) | 31 |
| 38 | 12 | $Me_2CO$ | reflux | 18 | 12a (71) | 44 |
| 39 | 13 | $Me_2CO$ | reflux | 18 | 13a (70) | 45 |
| 40 | 14 | $Me_2CO$ | reflux | 18 | 14a (73) | 59 |
| 41 | 15 | $Me_2CO$ | reflux | 15 | 15a (76) | 49 |
| 42 | 16 | $Me_2CO$ | reflux | 15 | 16a (87) | 68 |
| 43 | 11 | PhCOMe | 80 | 15 | 11b (86) | 77 |
| 44 | 12 | PhCOMe | 80 | 15 | 12b (74) | 68 |
| 45 | 13 | PhCOMe | 80 | 15 | 13b (82) | 66 |
| 46 | 14 | PhCOMe | 80 | 15 | 14b (85) | 80 |
| 47 | 15 | PhCOMe | 80 | 10 | 15b (74) | 71 |
| 48 | 16 | PhCOMe | 80 | 12 | 16b (76) | 49 |

[a]Reaction conditions: 0.5 mmol substrate, 0.5 mmol $Fe(NO_3)_3$, 3.0 mL solvent
[b]Yield: GLC yield (%)

Spectrum Data

Of the compounds (11a to 16a and 11b to 16b) isolated and purified in Working Examples 37 to 48, the spectrum data is given below for novel compounds (11a to 13a and 11b to 13b).

3-acetyl-5-propylisoxazole (11a): pale yellow, oily substance

IR (KBr): 1705 and 1593 cm$^{-1}$ $^1$H-NMR (CDCl$_3$): δ (ppm) 6.36 (s, 1H), 2.75-2.79 (t, 2H), 2.63 (s, 3H), 1.70-1.80 (m, 2H), and 0.98-1.02[6] (t, 3H) $^{13}$C-NMR (CDCl$_3$): δ (ppm) 192.4, 175.4, 162.1, 99.2, 28.6, 27.2, 20.8, and 13.5 CI-MS: m/z 154 [M+H]$^+$ EI-MS: m/z 153 (1.44), 138 (0.87), 124 (0.07), 109 (0.06), 83 (0.21), and 67 (0.74) HR-MS Found: m/z 157.0788 [M]$^+$. Calculated for $C_8H_{11}NO_2$: M, 157.0790.

3-acetyl-5-butylisoxazole (12a): pale yellow, oily substance

IR (KBr): 1706 and 1593 cm$^{-1}$ $^1$H-NMR (CDCl$_3$): δ (ppm) 6.36 (s, 1H), 2.78-2.82 (t, 2H), 2.63 (s, 3H), 1.66-1.74 (m, 2H), 1.35-1.45 (m, 2H), and 0.93-0.96 (t, 3H) $^{13}$C-NMR (CDCl$_3$): δ (ppm) 192.4, 175.6, 162.1, 99.1, 29.4, 27.2, 26.3, 22.1, and 13.6 CI-MS: m/z 168 [M+H]$^+$ EI-MS: m/z 167 (0.55), 152 (0.47), 124 (0.86), 98 (0.44), 83 (0.34), 68 (1.18), 57 (0.66), and 43 (100) HR-MS Found: m/z 167.0909 [M]$^+$. Calculated for $C_9H_{13}NO_2$: M, 167.0946.

3-acetyl-5-pentylisoxazole (13a): pale yellow, oily substance

IR (KBr): 1707 and 1593 cm$^{-1}$ $^1$H-NMR (CDCl$_3$): δ (ppm) 6.36 (s, 1H), 2.77-2.81 (t, 2H), 2.63 (s, 3H), 1.68-1.76 (m, 2H), 1.33-1.37 (m, 4H), and 0.89-0.92 (t, 3H) $^{13}$C-NMR (CDCl$_3$): δ (ppm) 192.4, 175.6, 162.1, 99.1, 31.1, 27.2, 26.6, 22.2, and 13.9 CI-MS: m/z 182 [M+H]$^+$ EI-MS: m/z 181 (0.45), 166 (0.37), 138 (0.38), 120 (0.19), 97 (0.13), 83 (0.32), 68 (1.11), 55 (0.97), and 43 (100) HR-MS Found: m/z 181.1097 [M]$^+$. Calculated for $C_{10}H_{15}NO_2$: M, 181.1103.

3-benzoyl-5-propylisoxazole (11b): pale yellow, oily substance

IR (KBr): 1663 and 1597 cm$^{-1}$ $^1$H-NMR (CDCl$_3$): δ (ppm) 7.47-8.30 (m, 5H), 6.51 (s, 1H), 2.78-2.82 (t, 2H), 1.72-1.83 (m, 2H), and 0.99-1.03 (t, 3H) $^{13}$C-NMR (CDCl$_3$): δ (ppm) 185.9, 174.3, 161.7, 135.7, 133.7, 130.4, 128.3, 101.5, 28.3, 20.7, and 13.4 CI-MS: m/z 216 [M+H]$^+$ EI-MS: m/z 215 (1.22), 144 (0.25), 116 (0.27), 105 (100), 77 (64.45), 63 (0.84), and 51 (33.66) HR-MS Found: m/z 215.0924 [M]$^+$. Calculated for $C_{13}H_{13}NO_2$: M, 215.0946.

3-benzoyl-5-butylisoxazole (12b): pale yellow, oily substance

IR (KBr): 1663 and 1597 cm$^{-1}$ $^1$H-NMR (CDCl$_3$): δ (ppm) 7.47-8.30 (m, 5H), 6.51 (s, 1H), 2.80-2.84 (t, 2H), 1.68-1.76 (m, 2H), 1.37-1.46 (m, 2H), and 0.91-0.96 (t, 3H) $^{13}$C-NMR (CDCl$_3$): δ (ppm) 185.9, 174.5, 161.7, 135.7, 133.7, 130.4, 128.3, 101.4, 29.3, 26.1, 21.9, and 13.5 CI-MS: m/z 230 [M+H]$^+$ EI-MS: m/z 229 (0.95), 144 (0.22), 115 (0.20), 105 (100), 89 (0.51), 77 (54.90), 55 (0.80), and 51 (25.47) HR-MS Found: m/z 229.1062 [M]$^+$. Calculated for $C_{14}H_{15}NO_2$: M, 229.1103.

3-benzoyl-5-pentylisoxazole (13b): pale yellow, oily substance

IR (KBr): 1663 and 1598 cm$^{-1}$ $^1$H-NMR (CDCl$_3$): δ (ppm) 7.45-8.30 (m, 5H), 6.50 (s, 1H), 2.77-2.81 (t, 2H), 1.68-1.76 (m, 2H), 1.33-1.36 (m, 4H), and 0.87-0.91 (t, 3H) $^{13}$C-NMR (CDCl$_3$): δ (ppm) 185.7, 174.4, 161.6, 135.6, 133.6, 130.3, 128.2, 101.3, 30.9, 26.8, 26.2, 22.0, and 13.6 CI-MS: m/z 244 [M+H]$^+$ EI-MS: m/z 243 (0.73), 144 (0.18), 115 (0.20), 105 (100), 89 (0.43), 77 (48.54), 55 (1.54), and 51 (20.52) HR-MS Found: m/z 243.1226 [M]$^+$. Calculated for $C_{15}H_{17}NO_2$: M, 243.1259.

Next, isoxazole derivatives were synthesized using iron (III) nitrate obtained using ethynyltestosterone as the substrate. Synthesizing isoxazole derivatives from ethynyl compounds having a steroid skeleton took a long time in the reaction, and the yield was low.

In view of this, the inventors conducted a test in which they irradiated the system with microwaves during the reaction so as to shorten the reaction time in the synthesis of an isoxazole derivative from ethynyltestosterone having an ethynyl group on a side chain of the following structure, and to raise the yield.

[Reaction Formula 1]

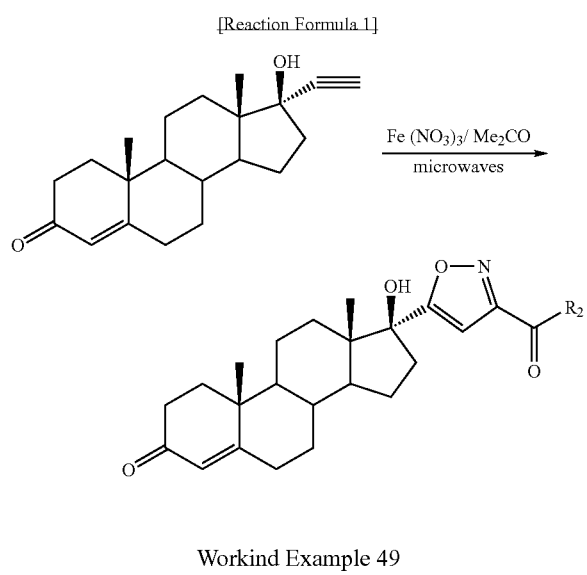

Workind Example 49

(6) Synthesizing isoxazole derivative from ethynyltestosterone 1.5 equivalents (with respect to the substrate) of iron(III) nitrate and 5 mL of acetone were mixed in a sealed test tube for microwaves, and a reaction was conducted in microwaves. These microwaves had an output of 250 watts (W) and a pressure of 15 bar, and an isoxazole derivative was synthesized using the ethynyltestosterone expressed by the above Reaction Formula 1 above at a reaction temperature of 150° C. and for a reaction time of 30 minutes (20 minute run time and 10 minute hold time). After the reaction, the product was filtered through a High-Flow Super Cell to remove the metal salt. This was extracted with diethyl ether. After this, the extract was washed first with saturated sodium hydrogencarbonate, then with saturated salt water, then with distilled water, the ether layer was dried and concentrated with anhydrous sodium sulfate, and then this product was isolated and purified by column chromatography, and the compound was identified by IR, $^1$H-NMR, $^{13}$C-NMR, and GC-MS.

When microwaves were used in the above reaction, an isoxazole derivative was obtained at an isolation yield of 19%. However, under ordinary reflux conditions involving no microwave irradiation, the isolation yield was only 8% at a reaction time of 20 hours.

It was found from the above that an isoxazole derivative can be obtained at a better yield and in a shorter time using microwaves than when heating is merely performed under reflux condition.

The following device was used in Working Example 49.

Microwave Discover (CEM)

The following measurement apparatus were used in determining the structure of the product.

IR: FT-IR-230 (JASCO)
NMR: JEOL GSX400 (JEOL)
GC: Shimadzu Gas Chromatograph GC-17A (Shimadzu)
GC-MS: GCMS-QP5050 (Shimadzu)

Spectrum Data

The isoxazole derivative isolated and purified from ethynyltestosterone in Working Example 49 was a novel compound, and the spectrum data thereof is given below.

3-acetyl-5-(17'-testosteryl)isoxazole: pale yellow crystals with a melting point of 98 to 100° C.

IR (NaCl): 3440, 1706, 1654, and 1542 cm$^{-1}$ $^1$H-NMR (CDCl$_3$): δ=6.52 (s, 1H), 5.71 (s, 1H), and 2.64 (s, 3H) $^{13}$C-NMR (CDCl$_3$): δ=203.9, 191.0, 161.2, and 83.3 EI-MS: m/z (%) 397 [M]$^+$ (1), 382 [M-CH$_3$]$^+$ (1), 355 [M-CH$_3$CO]$^+$ (4), 269 [M-C$_5$H$_5$NO$_3$]$^+$ (1), 244 [M-C$_7$H$_7$NO$_3$]$^+$ (2), 43 [M-C$_{22}$H$_{28}$NO$_3$]$^+$ (100) HR-MS Found: m/z 397.2256 [M]$^+$. Calculated for C$_{24}$H$_{31}$NO$_4$: M, 397.2253.

Reaction Formula 2 below shows the reaction mechanism in Working Example 49.

[Reaction Formula 2]

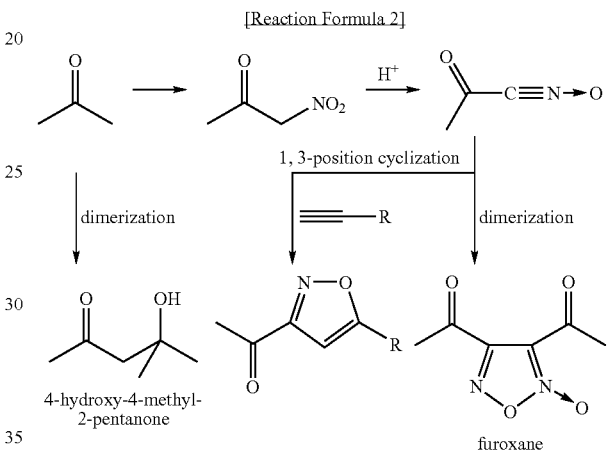

Specifically, the methyl group in the alpha position of the acetone used as the solvent is nitrated to produce nitroketone. This nitroketone is converted in the presence of a proton into nitrile oxide. This nitrile oxide and the alkyne undergo a 1,3-dipolar cycloaddition reaction to produce an isoxazole derivative. If no alkyne is present, the nitrile oxide forms a dimer and produces furoxane.

The above results revealed the following.

(1) There is no major change in the yield beyond a reaction time of 30 minutes.

(2) The yield is best when the iron(III) nitrate is used in an amount of 1.5 equivalents.

(3) The reaction temperature must be high in order to increase the yield of the product.

(4) The targeted product is obtained with fewer byproducts when iron(III) nitrate is used than when CAN(IV) is used.

The above results tell us that the microwaves promoted the reaction, and the product was obtained more efficiently and in a shorter time.

The reaction conditions, reaction reagents, chemical equivalent of acetone, reaction mechanism, and yield in the present invention will now be investigated.

Investigation of Reaction Conditions

The reaction was conducted by varying the equivalents of iron nitrate to examine the proportion of iron(III) nitrate actually used with respect to the substrate at which the reaction will proceed most efficiently.

As a result, as shown in Table 6 below, it was found that the yield was 85% when the iron(III) nitrate was used in an amount of 1 molar equivalent with respect to the substrate, and the yield was 84% when the amount was 1.5 molar equivalents, and that the targeted isoxazole derivative was obtained at the highest yield when 1 molar equivalent was used.

In light of the above, it is possible that if there is too little iron(III) nitrate, a lack of reaction reagent could be the cause of the low yield. As for the poor yield if there is too much iron(III) nitrate, the main reason may be that there is not enough 1-alkene compound (the substrate) as a result of the production of nitroalkenes, nitroalcohols, or the like (discussed below) as byproducts, or a breakdown of the isoxazole skeleton formed by the iron(III) nitrate having oxidizing power and present in an excess quantity in the reaction system.

TABLE 6

Reacting 1-octene and $Fe(NO_3)_3$ in acetone 3, 3a: $R_1$ = n-$C_6H_{13}$, $R_2$ = $CH_3$

| Working Example[a] | $Fe(NO_3)_3$ (molar equivalents) | Time (hours) | Product (%)[b] |
|---|---|---|---|
| 1 | 0.1 | 55 | no reaction |
| 2 | 0.5 | 25 | 3a (44) |
| 3 | 1.0 | 25 | 3a (85) |
| 4 | 1.5 | 15 | 3a (84) |
| 5 | 2.0 | 10 | 3a (75) |
| 6 | 4.0 | 10 | 3a (68) |

[a]Reaction conditions: 0.5 mmol 1-octene, 0.1 to 4.0 molar equivalents $Fe(NO_3)_3$, 4.0 mL acetone
[b]Yield: GLC yield (%)

Investigation of Reaction Reagents

Comparative Experiment

The synthesis of an isoxazole derivative using cerium ammonium nitrate (CAN) has already been reported, and this report also suggests that the nitrogen atom in the 2-position of the isoxazole ring originates in a nitric acid ion. Because of this, it was hoped that the reaction would proceed when using a nitrate other than CAN, and various nitrates were studied.

These results are given in Table 7 below. No reaction progress was observed with ammonium nitrate (not a metal salt), aluminum salts, or magnesium salts. In a reaction using cerium(III) ammonium nitrate (CAN(III)), which has already been reported, the reaction proceeds when formic acid is added, so the addition of formic acid was also investigated with the above nitrates, but no reaction progress was observed. The reaction was confirmed to proceed with a copper salt, but the yield thereof was low. The result of these investigations was that when iron(III) nitrate was used, an isoxazole derivative was obtained at the same or higher yield as when cerium ammonium nitrate (CAN) was used.

Based on previous reports, it is conceivable that the effect had by formic acid is that it works as a proton source when using a metal having no oxidizing power. With iron(III) nitrate, which does have oxidizing power, the production of protons in the solvent is possible, so the supply of protons by formic acid is believed to have little effect on the yield. On the other hand, part of the iron(III) nitrate is believed to be reduced by the reducing power had by formic acid, which hampers the progress of the reaction, and the result of this is believed to be a decrease in yield. With copper(II) nitrate, it is believed that a complex is formed between the Cu(II) and the isoxazole ring that is produced, and since the role of formic acid is to take out an isoxazole ring that was incorporated as a ligand, there is an increase in yield.

TABLE 7

Reacting a 1-octene compound obtained using various nitrates in acetone 3, 3a: $R_1$ = n-$C_6H_{13}$, $R_2$ = $CH_3$

| Experiment Number | Nitrate | Product (%)[c] |
|---|---|---|
| 1[a] | CAN (IV) | 3a (72) |
| 2[b] | CAN(III)—HCOOH | 3a (84) |
| 3[a] | $NH_4NO_3$ | no reaction |
| 4[a] | $Mg(NO_3)_2$ | no reaction |
| 5[b] | $Mg(NO_3)_2$—HCOOH | no reaction |
| 6[a] | $Al(NO_3)_3$ | no reaction |
| 7[b] | $Al(NO_3)_3$—HCOOH | no reaction |
| 8[a] (Present invention) | $Fe(NO_3)_3$ | 3a (85) |
|  | $Fe(NO_3)_3$—HCOOH | 3a (77) |
|  | $Cu(NO_3)_2$ | 3a (22) |
| 9[b] | $Cu(NO_3)_2$—HCOOH | 3a (52) |
| 10[a] |  |  |
| 11[b] |  |  |

[a]Reaction conditions: 0.5 mmol 1-octene, 0.5 mmol nitrate, and 3.0 mL acetone, under reflux
[b]Reaction conditions: 0.5 mmol 1-octene, 0.5 mmol nitrate, 5 mmol formic acid, and 3.0 mL acetone, under reflux
[c]Yield: GLC yield (%)

Stoichiometric Investigation of Acetone

In this reaction, the acetone solvent also participates in the reaction, so to examine the effect that changes in the acetone equivalents has on the reaction, a test was conducted in which acetonitrile was used as a solvent, and the equivalents of acetone with respect to the substrate were varied.

Also, when acetophenone is used as the solvent, it has to be distilled off under reduced pressure, so it is preferable to reduce the amount thereof as much as possible. In this respect, it is probably significant to study what effect acetone or acetophenone has on the yield at a substrate amount. As discussed below regarding the reaction mechanism, acetone and acetophenone are both involved in isoxazole ring formation through the same mechanism, so acetone was used in this experiment, but the investigation was conducted on the premise that the tendency would be the same if acetophenone were used.

As a result, as shown in Table 8 below, if there are too few equivalents of acetone, a nitroalkene (3a') or nitroalcohol (3a"), which are byproducts, will be obtained, but it was found that the production of these byproducts is suppressed, and the amount of isoxazole derivative produced increases, as the equivalents of acetone increase. When iron(III) nitrate was used, the proportions in which 3a' and 3a" were produced were lower than that of cerium(IV) ammonium nitrate (CAN (IV)). This also explains the better yield of isoxazole derivative when iron(III) nitrate is used.

TABLE 8

Relationship of acetone equivalents in 1-octene reaction in presence of Fe(NO₃)₃ in acetonitrile

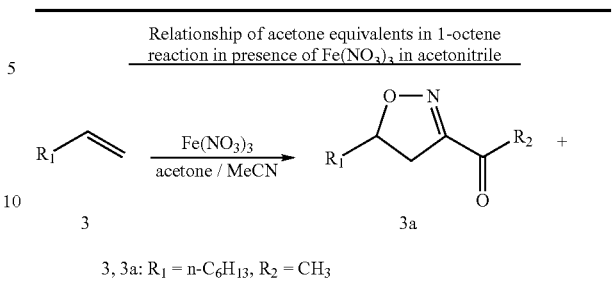

3, 3a: R₁ = n-C₆H₁₃, R₂ = CH₃

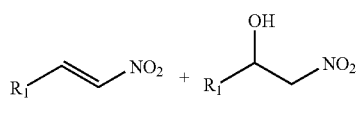

| Experiment Number | Acetone (molar equivalents) | Product (%)[b] |
|---|---|---|
| 1 | — | 3a (trace) 3a' (15) 3aΔ (6) |
| 2 | 1.0 | 3a (3) 3a' (23) 3a" (15) |
| 3 | 5.0 | 3a (20) 3a' (24) 3a" (24) |
| 4 | 10 | 3a (47) 3a' (18) 3a" (22) |
| 5 | 20 | 3a (66) 3a' (12) 3a" (16) |
| 6 | 30 | 3a (67) 3a' (9) 3a" (10) |
| 7 | 40 | 3a (72) 3a' (7) 3a" (8) |
| 8 | 50 | 3a (75) 3a' (6) 3a" (8) |

[a]Reaction conditions: 0.5 mmol 1-octene, 0.5 mmol Fe(NO₃)₃, 0 to 50.0 molar equivalents acetone, 4.0 mL acetonitrile, under reflux for 25 hours
[b]Yield: GLC yield (%)

Reaction Mechanism

The reaction mechanism in each of the above reactions is believed to be the same as that when cerium ammonium nitrate (CAN) is used, as shown by the reaction mechanism below. The methyl group in the alpha position of the carbonyl compound used as the solvent is nitrated, and the action of a proton produces nitrile oxide from this nitro group. Here, the nitrile oxide produced when acetophenone is used may be more stable than the nitrile oxide produced from acetone, so it is believed that the 1,3-dipolar cycloaddition reaction with the carbon-carbon unsaturated bond position of the 1-alkene compound, 1-alkyne compound, or the like occurs more efficiently, and the product is obtained at a better yield.

[Reaction Formula 3]

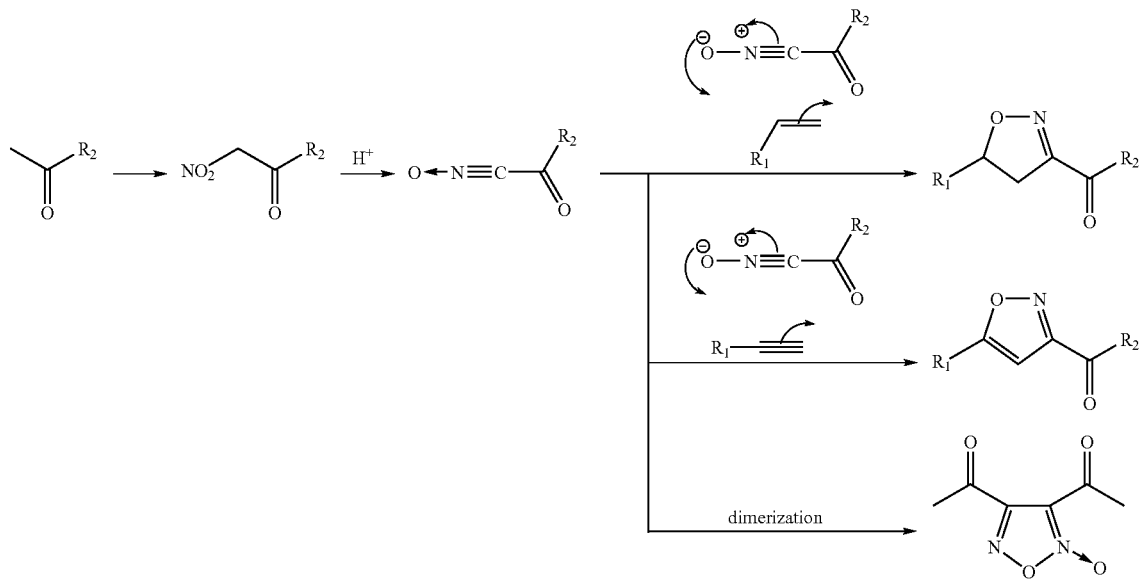

It has been reported that nitrile oxide produced from acetone will dimerize and produce furoxane unless a 1-alkene compound or 1-alkyne compound is present. Since it was confirmed here that furoxane was produced in the absence of a 1-alkene compound or 1-alkyne compound in a reaction in which iron(III) nitrate was used, it is possible that nitrile oxide was produced. This also suggests that the reaction proceeds by the same mechanism as when cerium ammonium nitrate (CAN) is used.

Difference in Yield when Acetone and Acetophenone are Used

It was found that the targeted isoxazole derivative was obtained at a higher yield when acetophenone was used than when acetone was used. The reason for this may be the stability of the nitrile oxide stage, which is a reaction intermediate. Nitrile oxide produced from acetone is unstable, undergoes a dimerization reaction, and produces furoxane, but nitrile oxide produced from acetophenone is stable and therefore does not undergo a dimerization reaction, so no furoxane is produced. If we look at the far-right structure in the following resonance structure formula, we see that whereas nitrile oxide produced from acetone has a methyl group next to a positive charge, the nitrile oxide produced from acetophenone has a phenyl group, which has a powerful electron delocalizing ability, next to a positive charge. This also leads to the belief that nitrile oxide produced from acetophenone is more stable.

-continued

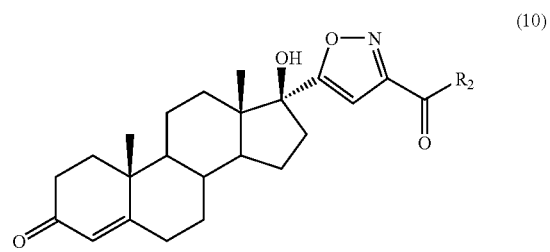

(10)

(where $R_2$ is a methyl group or a phenyl group).

2. A compound expressed by Formula (10):

[Reaction Formula 4]

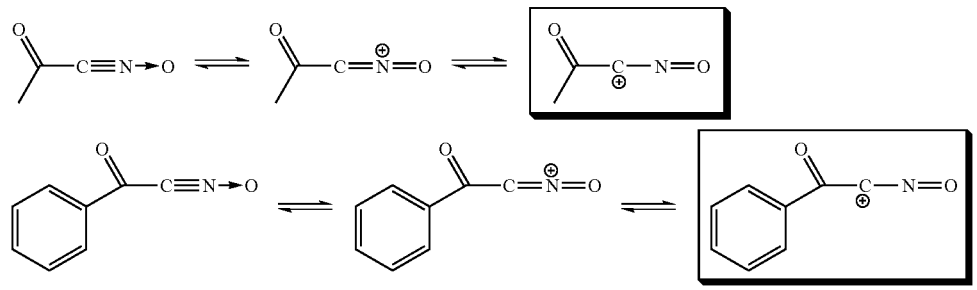

What is claimed is:

1. A method for manufacturing a compound expressed by Formula (10) comprising the step of:

reacting an ethynyltestosterone compound expressed by Formula (9) with iron(III) nitrate under microwave irradiation in the presence of acetone or acetophenone to thereby form the compound expressed by Formula (10):

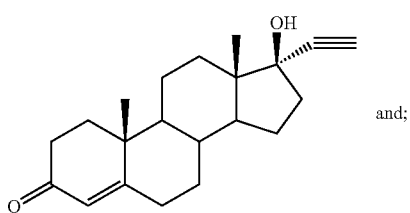

(9)

and;

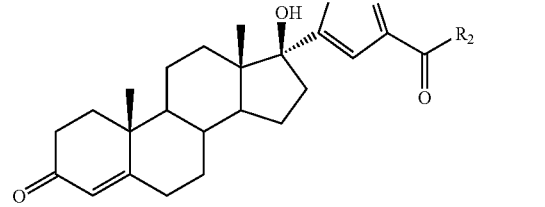

(10)

(where $R_2$ is a methyl group or a phenyl group).

3. The compound according to claim 2, wherein $R_2$ is a methyl group.

4. The compound according to claim 2, wherein $R_2$ is a methyl group or a phenyl group.

* * * * *